United States Patent [19]

Maurer et al.

[11] Patent Number: 4,489,088
[45] Date of Patent: Dec. 18, 1984

[54] N,N-DIMETHYL O-(1-CARBAMOYL-PYRAZOL-5-YL) CARBAMATES AS PEST-COMBATING AGENTS

[75] Inventors: Fritz Maurer, Wuppertal; Ingeborg Hammann, Muelheim; Bernhard Homeyer, Leverkusen, all of Fed. Rep. of Germany

[73] Assignee: Bayer Aktiengesellschaft, Leverkusen, Fed. Rep. of Germany

[21] Appl. No.: 458,126

[22] Filed: Jan. 14, 1983

[30] Foreign Application Priority Data

Jan. 27, 1982 [DE] Fed. Rep. of Germany ....... 3202625

[51] Int. Cl.³ .................. A01N 43/56; C07D 231/20
[52] U.S. Cl. ................ 424/273 P; 548/367; 548/377
[58] Field of Search .............. 548/377, 367, 116; 424/273 P

[56] References Cited

U.S. PATENT DOCUMENTS 3,452,043  6/1969  Grauer et al. ............ 548/377
3,723,456  3/1973  Fest et al. .............. 548/116
4,126,690 11/1978  Maurer et al. ........... 548/377
4,215,132  7/1980  Maurer et al. ........... 548/377
4,307,107 12/1981  Maurer et al. ........... 548/367

FOREIGN PATENT DOCUMENTS 0009634  4/1980  European Pat. Off. ....... 548/377
0017066 10/1980  European Pat. Off. ....... 548/377
1404687  5/1965  France ................... 548/377

Primary Examiner—Henry R. Jiles
Assistant Examiner—Kurt G. Briscoe
Attorney, Agent, or Firm—Sprung, Horn, Kramer & Woods

[57] ABSTRACT

N,N-dimethyl O-(1-carbamoyl-pyrazol-5-yl) carbamates of the formula

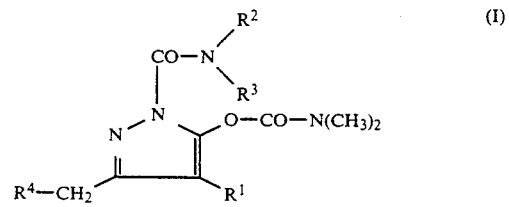

in which $R^1$, $R^2$ and $R^3$, independently of one another, represent a hydrogen atom or an optionally substituted alkyl group, and $R^4$ represents an alkoxy, alkylthio, alkylsulphinyl or alkylsulphonyl group, are new and are obtained when a 5-hydroxy-pyrazole of the general formula

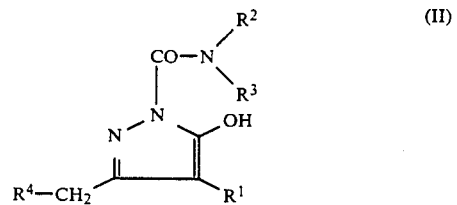

or an alkali metal salt or alkaline earth metal salt thereof, is reacted with an N,N-dimethyl-carbamic acid-halide of the general formula

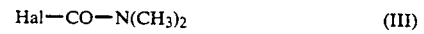

in which Hal represents a chlorine or bromine atom. The compounds of formula (I) can be used as pest-combating agents, especially in combating insects or acarids.

11 Claims, No Drawings

N,N-DIMETHYL O-(1-CARBAMOYL-PYRAZOL-5-YL) CARBAMATES AS PEST-COMBATING AGENTS

The invention relates to certain new N,N-dimethyl O-(1-carbamoyl-pyrazol-5-yl) carbamates, to a process for their production, and to their use as pest-combating agents, especially as insecticides.

It has been disclosed that certain N,N-dimethyl O-pyrazolyl carbamates, such as N,N-dimethyl O-(1-phenyl-3-methyl-pyrazol-5-yl) carbamate and N,N-dimethyl O-(1-isopropyl-3-methyl-pyrazol-5-yl) carbamate, possess insecticidal properties (see Swiss Patent Specification No. 279,553). However, the insecticidal action of these known compounds is not always satisfactory, in particular in the case of low active compound concentrations and use amounts.

The present invention now provides, as new compounds, the N,N-dimethyl O-(1-carbamoyl-pyrazol-5-yl) carbamates of the general formula

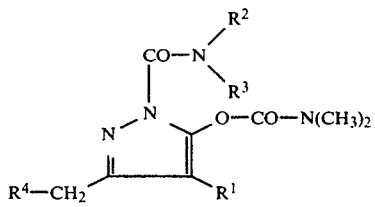

in which

R$^1$, R$^2$ and R$^3$, independently of one another, represent a hydrogen atom or an optionally substituted alkyl group, and R$^4$ represents an alkoxy, alkylthio, alkylsulphinyl or alkylsulphonyl group.

According to the present invention, we further provide a process for the production of a compound of the present invention, characterized in that a 5-hydroxy-pyrazole of the general formula

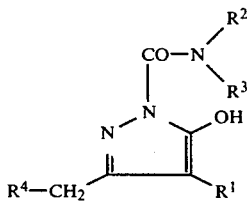

in which R$^1$, R$^2$, R$^3$ and R$^4$ have the meanings given above, or an alkali metal salt or alkaline earth metal salt thereof, is reacted with an N,N-dimethyl-carbamic acid-halide of the general formula

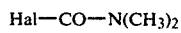

in which Hal represents a chlorine or bromine atom, if appropriate in the presence of an acid acceptor and, if appropriate, using an inert diluent.

The new N,N-dimethyl O-(1-carbamoyl-pyrazol-5-yl) carbamates of the formula (I) are distinguished by high activity as pest-combating agents, in particular by their outstanding insecticidal action.

Surprisingly, the N,N-dimethyl O-(1-carbamoyl-pyrazol-5-yl) carbamates according to the invention exhibit a substantially higher insecticidal action than the N,N-dimethyl O-pyrazolyl carbamates, such as N,N-dimethyl O-(1-phenyl-3-methyl-pyrazol-5-yl) carbamate and N,N-dimethyl O-(1-isopropyl-3-methyl-pyrazol-5-yl) carbamate, which are known from the prior art and are compounds of analogous constitution and identical direction of action.

Preferred compounds of the present invention are those, in which

R$^1$, R$^2$ and R$^3$, independently of one another, represent a hydrogen atom or a straight-chain or branched alkyl group having 1 to 6 carbon atoms, and R$^4$ represents an alkoxy, alkylthio, alkylsulphinyl or alkylsulphonyl group, each having a straight-chain or branched alkyl radical which has 1 to 6 carbon atoms.

Very particularly preferred compounds of the present invention are those in which R$^1$ represents a hydrogen atom or a methyl, ethyl, n-propyl or iso-propyl group, R$^2$ and R$^3$, independently of each other, represent a hydrogen atom or a methyl, ethyl, n-propyl, isopropyl, n-butyl or iso-butyl group, and R$^4$ represents a methoxy, ethoxy, n-propoxy, isopropoxy, n-butoxy, iso-butoxy, sec-butoxy, methylthio, ethylthio, n-propylthio, iso-propylthio, n-butylthio, iso-butylthio, sec-butylthio, methylsulphinyl, ethylsulphinyl, n-propylsulphinyl, iso-propylsulphinyl, methylsulphonyl, ethylsulphonyl, n-propylsulphonyl or iso-propylsulphonyl group.

If, for example, 1-diethylcarbamoyl-3-methoxymethyl-5-hydroxypyrazole or the corresponding sodium salt and dimethylcarbamoyl chloride are used as starting materials for the process according to the invention, the corresponding reactions can be represented by the following equations:

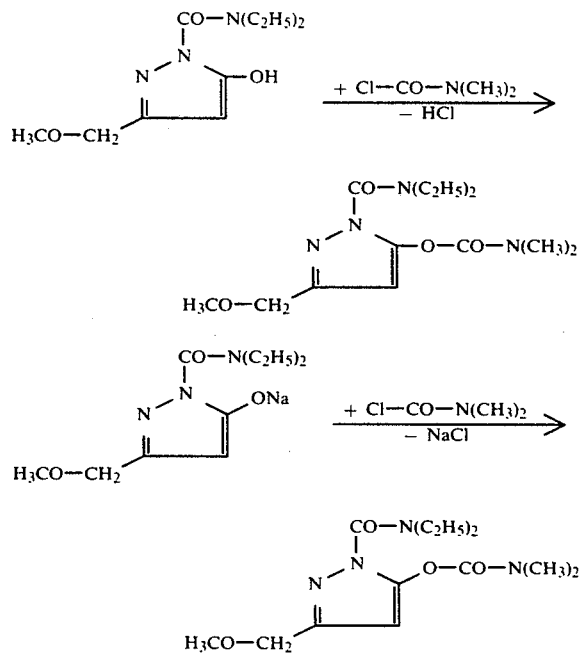

Preferred 5-hydroxy-pyrazoles of formula (II), or their alkali metal salts and alkaline earth metal salts, which are to be used as starting materials in the process according to the invention are those in which $R^1$, $R^2$, $R^3$ and $R^4$ represent those radicals which have been respectively mentioned in the definition of the preferred and very particularly preferred compounds of the invention, and, in the case of the salts, the alkali metal ion or alkaline earth metal ion represents a sodium ion, potassium ion, calcium ion or ammonium ion.

The 5-hydroxy-pyrazoles, or their alkali metal salts and alkaline earth metal salts, may be prepared by processes which are known in principle (see U.S. Pat. No. 4,126,690). They are obtained, for example, by reacting appropriate alkyl acetoacetate derivatives with hydrazine derivatives $H_2N-NH-CO-N(R^2)(R^3)$ ($R^2$ and $R^3$ have the meanings given above), at a temperature between 0° and 100° C., preferably between 20° and 80° C., if appropriate using alkali metal salts or alkaline earth metal salts (such as sodium sulphate), and if appropriate using a diluent (such as toluene) (see the preparative examples).

The alkyl acetoacetate derivatives to be employed as precursors for the preparation of the new compounds of the formula (I) are known (see, for example, U.S. Pat. Nos. 4,126,690 and 4,307,107).

The hydrazine derivatives to be employed as precursors for the preparation of the new compounds of the formula (I) are generally known compounds of organic chemistry.

The following may be mentioned as examples of the starting materials of the formula (II): 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-4-, -4-methyl-, -4-ethyl-, -4-n-propyl- and -4-isopropyl-1-carbamoyl-5-hydroxypyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-1-(di)-methylcarbamoyl-5-hydroxypyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-, -4-methyl-, -4-ethyl-, -4-n-propyl- and -4-isopropyl-1-(di)ethylcarbamoyl-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl-, and 3-isopropylsulphonylmethyl-4-methyl-, -4-ethyl-, -4-n-propyl- and -4-isopropyl-1-(di)-n-propylcarbamoyl-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl-, and 3-isopropylsulphonylmethyl-, -4-methyl-, -4-ethyl-, -4-n-propyl- and -4-isopropyl-1-(di)-isopropylcarbamoyl-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl-, and 3-isopropylsulphonylmethyl-, -4-methyl-, -4-ethyl-, -4-n-propyl- and -4-isopropyl-1-(methylethylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-, -4-methyl-, -4-ethyl-, -4-n-propyl- and -4-isopropyl-1-(methyl-n-propylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl-, and 3-isopropylsulphonylmethyl-, -4-methyl, -4-ethyl-, -4-n-propyl- and -4-isopropyl-1-(methyl-n-butylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl-, and 3-isopropylsulphonylmethyl-, -4-methyl-, -4-ethyl-, -4-n-propyl- and -4-isopropyl-1-(methyl-isobutylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-, -4-methyl-, -4-ethyl-, -4-n-propyl- and -4-isopropyl-1-(ethyl-n-propylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl-, and 3-isopropylsulphonylmethyl-, -4-methyl, -4-ethyl, -4-n-propyl- and -4-isopropyl-1-(ethyl-isopropylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl-, and 3-isopropylsulphonylmethyl-, -4-methyl-, -4-ethyl-, -4-n-propyl- and -4-isopropyl-1-(ethyl-n-butylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl-, and 3-isopropylsulphonylmethyl-, -4-methyl-, -4-ethyl-, -4-n-propyl- and -4-iso-propyl-1-(ethyl-isobutylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-, -4-methyl-, -4-ethyl-, -4-n-propyl- and -4-isopropyl-1-(n-propyl-isopropylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-iso-butylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-, -4-methyl-, -4-ethyl-, -4-n-propyl- and -4-isopropyl-1-(n-propyl-n-butylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-, -4-methyl-, -4-ethyl-, -4-n-propyl- and -4-isopropyl-1-(n-propyl-isobutylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-, -4-methyl-, -4-ethyl-, -4-n-propyl- and -4-isopropyl-1-(isopropyl-n-butylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl, -4-methyl-, -4-ethyl-, 4-n-propyl- and -4-isopropyl-1-(isopropyl-isobutylcarbamoyl)-5-hydroxy-pyrazole; 3-methoxymethyl-, 3-ethoxymethyl-, 3-n-propoxymethyl-, 3-isopropoxymethyl-, 3-n-butoxymethyl-, 3-isobutoxymethyl-, 3-sec-butoxymethyl-, 3-methylthiomethyl-, 3-ethylthiomethyl-, 3-n-propylthiomethyl-, 3-isopropylthiomethyl-, 3-n-butylthiomethyl-, 3-isobutylthiomethyl-, 3-sec-butylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-, -4-methyl-, -4-ethyl-, -4-n-propyl- and -4-isopropyl-1-(n-butyl-isobutylcarbamoyl)-5-hydroxy-pyrazole; and the corresponding sodium, potassium, calcium and ammonium salts.

N,N-dimethylcarbamic acid-chloride may be mentioned as an example of the carbamic acid-halides of the formula (III) which are to be used. N,N-dimethylcarbamic acid-chloride is a generally known compound of organic chemistry.

The process, according to the invention, for the preparation of the new N,N-dimethyl O-(1-carbamoyl-pyrazol-5-yl) carbamates is preferably carried out using diluents.

Suitable diluents are virtually any of the inert organic solvents. These include, especially, aliphatic and aromatic, optionally halogenated hydrocarbons (such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene), ethers, (such as diethyl ether and dibutyl ether, glycol dimethyl ether and diglycol dimethyl ether, tetrahydrofuran and dioxane), ketones (such as acetone, methyl ethyl ketone, methyl isopropyl ketone and methyl isobutyl ketone), esters (such as methyl acetate and ethyl acetate), nitriles (such as acetonitrile and propionitrile), amides (such as dimethylformamide, dimethylacetamide and N-methylpyrrolidone), and dimethyl sulphoxide, tetramethylenesulphone and hexamethylphosphoric acid triamide.

The process can, if appropriate, be carried out in the presence of acid acceptors. Suitable acid acceptors are any of the customary acid-binding agents. Those which have proved particularly suitable are alkali metal carbonates and alkali metal alcoholates (such as sodium carbonate and potassium carbonate, sodium methylate, sodium ethylate, potassium methylate and potassium ethylate), and also aliphatic, aromatic or heterocyclic amines (for example triethylamine, trimethylamine, dimethylaniline, dimethylbenzylamine and pyridine).

The process according to the invention is carried out in general at a temperature between 0° and 100° C. The range between 20° and 80° is preferred. The reactions are carried out in general under atmospheric pressure. To carry out the process according to the invention, the starting materials are usually employed in equimolar amounts. An excess of either of the reaction components has no substantial advantages. The reaction is carried out in general in a suitable diluent and, if appropriate, in the presence of an acid acceptor. After the end of the reaction, the mixture is poured into water, and extracted by shaking with an organic solvent, for example toluene. The organic phase is then worked up in the customary manner, by washing, drying and distilling off the solvent.

Some of the new compounds are obtained in the form of oils, which in some cases cannot be distilled without decomposition, but can be freed from the last volatile constituents by so-called "incipient distillation", that is to say by prolonged heating to moderately elevated temperatures under reduced pressure, and can be purified in this manner. They are characterized by their refractive indexes.

If the new products are obtained in a solid form after the solvent has been distilled off, they are purified by recrystallization. They are characterized by their melting points.

The active compounds are well tolerated by plants, have a favorable level of toxicity to warm-blooded animals, and are suitable for combating arthropod pests, especially insects and arachnida, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgara* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example, *Scutigerella immaculata;* from the order of the Thysanura, for example, *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix, Pemphigus* spp., *Pediculus humanus corporis, Haematopinus* spp. and *Linognathus* spp.;

from the order of the Mallophaga, for example *Trichodectes* spp. and *Damalinea* spp.;

from the order of the Thysanoptera, for example *Hercinothrips femoralis* and *Thrips tabaci;* from the order of the Heteroptera, for example *Eurygaster* spp., *Dysdercus intermedius, Piesma quadrata, Cimex lectularius, Rhodnius prolixus* and *Triatoma* spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humili, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia keuhniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the Hymenoptera, for example *Diprion* spp., *Hoplocampa* spp., *Lasius* spp., *Monomorium pharaonis* and *Vespa* spp.;

from the order of the Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hor-*

*tulanus, Oscinella frit, Phorbia* spp., *Pegomyia hyoscyami, Ceratitis capitata, Dacus oleae* and *Tipula paludosa;* from the order of the Siphonaptera, for example *Xenopsylla cheopis* and *Ceratophyllus* spp.;

from the class of the Arachnida, for example *Scorpio maurus* and *Latrodectus mactans;* from the order of the Acarina, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and vinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects and acarids) which comprises applying to the pests, or to a habitat thereof, a compound of the present invention alone or in the form of a composition containing as active ingredient a compound of the present invention in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The pesticidal activity of the compounds of this invention is illustrated by the following biotest examples.

In these examples, the compounds according to the present invention are each identified by the number (given in brackets) of the corresponding preparative example hereinbelow.

EXAMPLE A

Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The treated soil was filled into pots and these were planted with cabbage (Brassica oleracea). The active compound could in this way be taken up from the soil by the roots of the plants and be transported into the leaves.

To demonstrate the root-systemic effect, exclusively the leaves were infested with the abovementioned test insects after 7 days. After a further 2 days, the evaluation was made by counting or estimating the dead insects. The root-systemic action of the active compound was deduced from the mortality figures. It was 100% if all the test animals had been killed and 0% if just as many test insects were still alive as in the case of the untreated control.

In this test the following compounds, for example, showed a superior action compared to the prior art: (1), (2), (3) and (9).

EXAMPLE B

Myzus test
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (Brassica oleracea) which had been heavily infested with peach aphids (Myzus persicae) were treated by being dipped into the preparation of active compound of the desired concentration.

After the specified periods of time, the destruction in % was determined. 100% meant that all the aphids had been killed; 0% meant that none of the aphids had been killed.

In this test the following compounds, for example, showed a superior activity compared to the prior art: (1), (2) and (3).

PREPARATIVE EXAMPLES

EXAMPLE 1

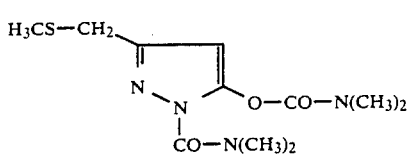

A mixture of 14.2 g (0.06 mol) of 1-dimethylcarbamoyl-3-methylthiomethyl-5-hydroxy-pyrazole sodium salt, 200 ml of acetonitrile and 6.5 g (0.06 mol) of dimethylcarbamoyl chloride was stirred for 3 hours at 55°–60° C. The reaction mixture was then cooled to 20° C., and filtered off under suction from the inorganic salt. The filtrate was evaporated down in vacuo. 14.3 g (83% of theory) of N,N-dimethyl O-(1-dimethyl-carbamoyl-3-methylthiomethyl-pyrazol-5-yl) carbmate remained in the form of beige crystals of melting point 36° C.

The following compounds of the formula (I)

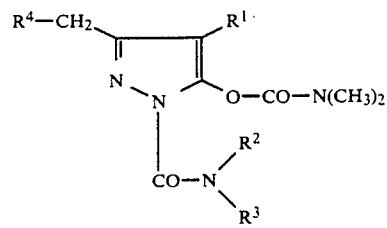

could be prepared in an analogous manner:

TABLE 1

| Example No. | $R^1$ | $R^2$ | $R^3$ | $R^4$ | Yield (% of theory) | Melting point (0° C.); refractive index |
|---|---|---|---|---|---|---|
| 2 | H | $CH_3$ | $CH_3$ | $CH_3SO$ | 72 | 88 |
| 3 | H | $CH_3$ | $CH_3$ | $CH_3SO_2$ | 77 | 118 |
| 4 | H | $CH_3$ | $CH_3$ | $C_2H_5S$ | | |
| 5 | $CH_3$ | $CH_3$ | $CH_3$ | $CH_3S$ | | |
| 6 | $CH_3$ | $CH_3$ | $CH_3$ | $CH_3SO$ | | |
| 7 | $CH_3$ | $CH_3$ | $CH_3$ | $CH_3-SO_2$ | | |
| 8 | H | $CH_3$ | H | $CH_3S$ | 30 | viscous oil |
| 9 | H | H | H | $CH_3S$ | 72 | $n_D^{20}$: 1.5410 |
| 10 | H | H | $C_2H_5$ | $CH_3S$ | | |
| 11 | H | $CH_3$ | $CH_3$ | $n$-$C_3H_7S$ | | |
| 12 | H | $CH_3$ | $CH_3$ | $CH_3O$ | | |
| 13 | H | $C_2H_5$ | $C_2H_5$ | $CH_3S$ | | |

Preparation of starting materials

The 5-hydroxy-pyrazoles, or their alkali metal salts or alkaline earth metal salts, which are to be used as precursors could be prepared, for example, as follows:

EXAMPLE 14

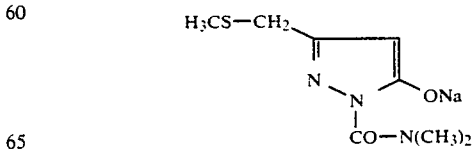

17.6 g (0.1 mol) of ethyl 4-methylthioacetoacetate were added to a solution of 10.3 g (0.1 mol) of 4,4-dimethylsemicarbazide in 50 ml of toluene at 30° to 35° C. After 4 hours, 8 g of sodium sulphate were added, the mixture was filtered, and 5.4 g (0.1 mol) of solid sodium methylate were added to the filtrate. The temperature of the mixture was kept at 20° to 25° C. during this operation. After 1 hour, 200 ml of ether were added, and the product was filtered off under suction after crystallization. 17 g (72% of theory) of 1-dimethylcarbamoyl-3-methylthiomethyl-5-hydroxy-pyrazole sodium salt of melting point 164° C.+ were obtained in this manner.

The following compounds of the formula (IIa)

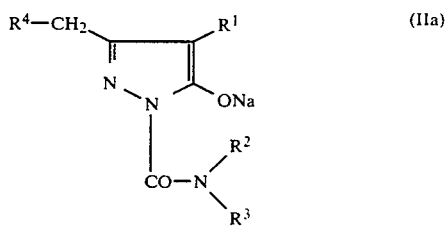

could be prepared in an analogous manner:

TABLE 2

| Example No. | $R^1$ | $R^2$ | $R^3$ | $R^4$ | Yield (% of theory) | Physical constant (refractive index); melting point [0°] |
|---|---|---|---|---|---|---|
| 15 | H | $CH_3$ | $CH_3$ | $C_2H_5S$ | | |
| 16 | $CH_3$ | $CH_3$ | $CH_3$ | $CH_3S$ | | |
| 17 | H | $CH_3$ | H | $CH_3S$ | 92 | 132+ |
| 18 | H | H | H | $CH_3S$ | 80 | 145+ |
| 19 | H | H | $C_2H_5$ | $CH_3S$ | | |
| 20 | H | $CH_3$ | $CH_3$ | $n-C_3H_7S$ | | |
| 21 | H | $CH_3$ | $CH_3$ | $CH_3O$ | | |
| 22 | H | $C_2H_5$ | $C_2H_5$ | $CH_3S$ | | |

The physical constants are given for the free hydroxy-pyrazoles, which could be obtained by acidification of the aqueous solution of the sodium salts.

It will be understood that the specification and examples are illustrative but not limitative of the present invention and that other embodiments within the spirit and scope of the invention will suggest themselves to those skilled in the art.

We claim:

1. An N,N-dimethyl O-(1-carbamoyl-pyrazol-5-yl) carbamate of the formula

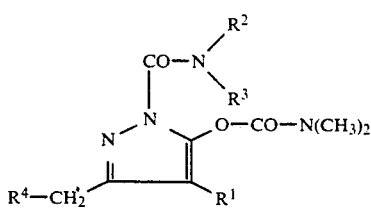

in which
$R^1$, $R^2$ and $R^3$ each independently is a hydrogen atom or an alkyl group having 1 to 6 carbon atoms, and
$R^4$ is an alkoxy, alkylthio, alkylsulphinyl or alkylsulphonyl group which has 1 to 6 carbon atoms.

2. A compound according to claim 1, in which
$R^1$ is a hydrogen atom or a methyl, ethyl, n-propyl or iso-propyl group,
$R^2$ and $R^3$ each independently is a hydrogen atom or a methyl, ethyl, n-propyl, iso-propyl, n-butyl or iso-butyl group, and
$R^4$ is a methoxy, ethoxy, n-propoxy, isopropoxy, n-butoxy, iso-butoxy, sec-butoxy, methylthio, ethylthio, n-propylthio, iso-propylthio, n-butylthio, iso-butylthio, sec-butylthio, methylsulphinyl, ethylsulphinyl, n-propylsulphinyl, iso-propylsulphinyl, methylsulphonyl, ethylsulphonyl, n-propylsulphonyl or iso-propylsulphonyl group.

3. A compound according to claim 1, wherein such compound is N,N-dimethyl O-(1-dimethyl-carbamoyl-3-methylthiomethyl-pyrazol-5-yl) carbamate of the formula

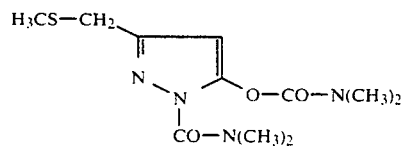

4. A compound according to claim 1, wherein such compound is N,N-dimethyl O-(1-dimethyl-carbamoyl-3-methylsulphinylmethyl-pyrazol-5-yl) carbamate of the formula

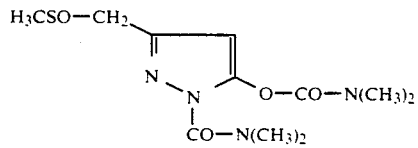

5. A compound according to claim 1, wherein such compound is N,N-dimethyl O-(1-dimethyl-carbamoyl-3-methylsulphonylmethyl-pyrazol-5-yl) carbamate of the formula

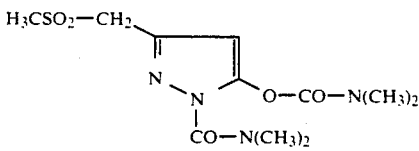

6. A compound according to claim 1, wherein such compound is N,N-dimethyl O-(1-methyl-carbamoyl-3-methylthiomethyl-pyrazol-5-yl) carbamate of the formula

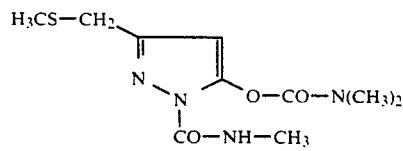

7. A compound according to claim 1, wherein such compound is N,N-dimethyl O-(1-carbamoyl-3-methylthiomethyl-pyrazol-5-yl) carbamate of the formula

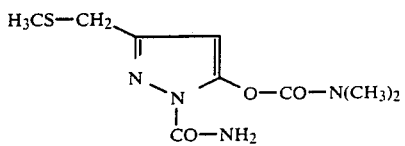

8. An insecticidal or acaridicidal composition comprising an insecticidally or acaridicidally effective amount of a compound according to claim 1 in admixture with a diluent.

9. A method of combatting insects or acarids, comprising applying to the insects or acarids, or to a habitat thereof, an insecticidally or acaridicidally effective amount of a compound according to claim 1.

10. The method according to claim 9, wherein such compound is

N,N-dimethyl O-(1-dimethyl-carbamoyl-3-methylthiomethyl-pyrazol-5-yl) carbamate, N,N-dimethyl O-(1-dimethyl-carbamoyl-3-methylsulphinylmethyl-pyrazol-5-yl) carbamate, N,N-dimethyl O-(1-dimethyl-carbamoyl-3-methylsulphonylmethyl-pyrazol-5-yl) carbamate, N,N-dimethyl O-(1-methyl-carbamoyl-3-methylthiomethyl-pyrazol-5-yl) carbamate or N,N-dimethyl O-(1-carbamoyl-3-methylthiomethyl-pyrazol-5-yl) carbamate.

11. A 5-hydroxy-pyrazole of the formula

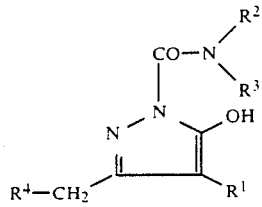

in which $R^1$, $R^2$ and $R^3$ each independently is a hydrogen atom or an alkyl group having 1 to 6 carbon atoms, and $R^4$ is an alkoxy, alkylthio, alkylsulphinyl or alkylsulphonyl group which has 1 to 6 carbon atoms.

* * * * *